(12) United States Patent
Akagawa et al.

(10) Patent No.: US 7,699,612 B2
(45) Date of Patent: Apr. 20, 2010

(54) METHOD FOR FIXING AN IMPLANT, FIXING MEMBER FOR THE IMPLANT AND IMPLANT COMPOSITE

(75) Inventors: Yasumasa Akagawa, Department of Advanced Prosthodontics Division of Cervico-Gnathomatology Programs for Applied Biomedicine Hiroshima University Graduate School of Biomedical Science Kasumi 1-2-3, Minami-ku, Hiroshima (JP); Takayasu Kubo, Hiroshima (JP); Kazuya Doi, Hiroshima (JP)

(73) Assignees: Yasumasa Akagawa, Hiroshima (JP); Covalent Materials Corporation, Tokyo (JP); MMT Co., Ltd., Osaka-shi (JP)

( * ) Notice: Subject to any disclaimer, the term of this patent is extended or adjusted under 35 U.S.C. 154(b) by 908 days.

(21) Appl. No.: 10/920,442

(22) Filed: Aug. 18, 2004

(65) Prior Publication Data
US 2005/0079469 A1 Apr. 14, 2005

(30) Foreign Application Priority Data
Aug. 21, 2003 (JP) ............................. 2003-297029

(51) Int. Cl.
*A61C 8/00* (2006.01)
(52) U.S. Cl. .................................. 433/173; 433/201.1
(58) Field of Classification Search ............... 623/17.17
See application file for complete search history.

(56) References Cited

U.S. PATENT DOCUMENTS

| | | | |
|---|---|---|---|
| 4,629,464 A | | 12/1986 | Takata et al. |
| 4,969,913 A | * | 11/1990 | Ojima ....................... 623/66.1 |
| 5,152,791 A | * | 10/1992 | Hakamatsuka et al. ... 623/23.56 |
| 5,456,601 A | | 10/1995 | Sendax |
| 5,716,359 A | * | 2/1998 | Ojima et al. ................... 606/76 |
| 6,048,344 A | | 4/2000 | Schenk |
| 6,149,688 A | * | 11/2000 | Brosnahan et al. .......... 623/23.5 |
| 6,340,648 B1 | * | 1/2002 | Imura et al. .................... 501/80 |
| 6,451,059 B1 | * | 9/2002 | Janas et al. ............... 623/23.51 |
| 6,458,162 B1 | * | 10/2002 | Koblish et al. ............ 623/23.51 |

(Continued)

FOREIGN PATENT DOCUMENTS

GB 2354519 A * 3/2001

(Continued)

*Primary Examiner*—David H Willse
*Assistant Examiner*—Javier G Blanco
(74) *Attorney, Agent, or Firm*—Foley & Lardner LLP

(57) ABSTRACT

A fixing member for an implant which comprises a tube or a pillar made of an hydroxyapatite ceramics at least one part of which is a ceramics porous article consisting essentially of a hydroxyapatite formed by agitation foaming, in which a number of approximately spherical pores mutually contact having pore structures communicated three-dimensionally opened at the contact area and having an averaged porosity of from 65% to 85%. A method for fixing an implant comprising a step of inserting an implant whose at least one part of the periphery is integrated with a hydroxyapatite ceramics into an implant insertion site of an alveolar bone or a gnathic bone. A method for fixing an implant, a fixing member for the implant and an implant composite in order to reinforce an implant insertion site by compensating or regenerating an alveolar bone or a gnathic bone on an implant treatment in dentistry or in oral surgery is obtained.

6 Claims, 2 Drawing Sheets

U.S. PATENT DOCUMENTS

2002/0022885 A1    2/2002   Ochi
2002/0104602 A1*   8/2002   Arai et al. ................ 156/89.11
2002/0155144 A1*  10/2002   Troczynski et al. ......... 424/423
2003/0138473 A1    7/2003   Koblish et al.

FOREIGN PATENT DOCUMENTS

| | | |
|---|---|---|
| JP | 6-197947 A | 7/1994 |
| JP | 2001-245903 A | 9/2001 |
| JP | 2003-507132 A | 2/2003 |
| WO | WO 98/38948 A1 | 9/1998 |
| WO | WO 9838948 A1 * | 9/1998 |
| WO | WO 03/007787 A2 | 1/2003 |

* cited by examiner

METHOD FOR FIXING AN IMPLANT, FIXING MEMBER FOR THE IMPLANT AND IMPLANT COMPOSITE

TECHNICAL FIELD

The present invention relates to a method for fixing an implant, a fixing member for the implant and an implant composite. In detail, it relates to a method for fixing an implant, a fixing member for the implant and an implant composite in order to reinforce an implant insertion site by compensating or regenerating an alveolar bone or a gnathic bone on an implant treatment in dentistry or in oral surgery.

BACKGROUND ART

Conventionally, it was general to apply an artificial denture or a bridge as a treatment method for the teeth loss area, edentulous area.

However, an implant treatment has been developed as a new dental treatment method in recent years and attracts attention. The implant treatment inserts a metal as an artificial tooth root into the alveolar bone or the gnathic bone and then, places an artificial tooth being similar with natural tooth over the metal making it as the foundation.

In comparison with the artificial denture, the implant tooth is superior in stability, and has enough biting force. Further, being different from the bridge, it is unnecessary for the implant tooth to give loads to other teeth or to whittle the adjacent healthy teeth in order to support itself, and it has advantages with no unnatural appearance and with capability of biting like the human's own tooth.

However, it is necessary for the implant treatment that the alveolar bone or the gnathic bone remains enough for supporting the implant tooth sufficiently.

The alveolar bone is an organ that depends upon tooth. Namely, the alveolar bone does not exist in a site without tooth, and does not form in the case where there is no tooth by nature. Moreover, without caring after exodontia makes the alveolar bone insensible against stimulation, absorbed and thinner.

Furthermore, caused by serious disease around teeth or accident and so on, the alveolar bone and the gnathic bone may be absorbed in circumferential textures or may be damaged.

Accordingly, it is difficult to insert the implant tooth with a condition as it is in the case where the alveolar bone or the gnathic bone is not sufficient in the amount or the situation.

Therefore, before carrying out the implant treatment, for example, a manipulation of increasing the thickness of an alveolar bone by means of a method referred to as a socket lift or a sinus lift in order to enable to insert a implant in the case where a palatine alveolar bone thinned.

Further, with regard to a mandible, well known is either an invention of compensating the thinned bone by filling granules of hydroxyapatite and so on or a manipulation of transplanting an own bone respectively into a site where the bone is poor.

By the way, the hydroxyapatite is a kind of calcium phosphate represented by a chemical formula $[Ca_{10}(PO_4)_6(OH)_2]$ and is an main composition composing bone, having adaptability with an own bone, etc., and further having properties of fixing into an organ in vivo by absorption after the lapse of time. Besides, the hydroxyapatite ceramics is widely employed as a suitable material for the artificial bone conventionally from the viewpoints of superior strength characteristic, advantage in the harmlessness to a living body.

U.S. Pat. No. 6,340,648 B1 discloses that a porous sintered body of ceramics which comprises spherical pores communicating with one another substantially throughout the body with relatively high porosity is preferable, among the hydroxyapatite ceramics, because osteoblast and related cells are easy to intrude into most of the pores and as a result, nutrients are supplied sufficiently to the cells.

Further, Japanese Patent Application Laid-Open No. 6(1994)-197947 proposes an implant, etc., formed by applying a ceramics coating of a crystallized glass mainly consisting of Diopside over the surface of a metallic substrate. The proposed implant is highly evaluated in its affinity with a living body and its mechanical strength.

Furthermore, Japanese Patent Application Laid-Open No. 2001-245903 proposes gnathic bone prosthesis materials having tooth root with simple structure, easily treatable, and giving capability of not only prosthesis of bone but also regeneration of tooth easily.

However, even the implant described in the Japanese Patent Application Laid-Open No. 6(1994)-197947 has a base metal for the implant itself remains covered by ceramics coating layer consisting of the crystallized glass. As described above, the ceramics being artifact, besides, being ceramics of the crystallized glass requires so long time until it functions as bone that a burden charged to a patient might be considerably great.

Further, it is extremely difficult to provide gnathic bone prosthesis materials having tooth root described in Japanese Patent Application Laid-Open No. 2001-245903 fitting a patient because it has a structure of preparedly inserting an implant into a compact apatite and at the same time, integrated with an artificial gnathic bone.

Accordingly, it is ideal that the implant is inserted directly in the own bone in order to support the implant stably and to obtain a good biocompatibility. Therefore, regarding with an implant insertion site, a practical patient-friendly technology for forming an alveolar bone or a gnathic bone sufficiently in the amount and the condition for strengthening the bone tissue was eagerly demanded.

SUMMARY OF THE INVENTION

The present invention is aimed for overcoming the foregoing technical problems. Namely, an object of the present invention is to provide a method for fixing an implant, a fixing member for the implant and an implant composite in order to reinforce an implant insertion site by compensating or reproducing an alveolar bone or a gnathic bone on an implant treatment in dentistry or in oral surgery.

The present invention provides a method for fixing an implant comprising steps of inserting a ceramics porous article consisting essentially of a hydroxyapatite into an implant insertion site of an alveolar bone or a gnathic bone reinforcing an own bone, and further inserting the implant into the own bone.

According to the method, compensation or regeneration and so on of the alveolar bone or the gnathic bone can be promoted, the bone tissue is strengthened, and the strength of the bone tissue can be increased swiftly to a degree of stably supporting the implant tooth.

Another aspect of the present invention provides a method for fixing an implant comprising a step of inserting an implant whose periphery is partially or entirely integrated with a hydroxyapatite ceramics containing at least one part of a porous article into an implant insertion site of an alveolar bone or a gnathic bone.

In this manner, the regeneration of bone can be further promoted by jointly using hydroxyapite ceramics in Guided Bone Regeneration (GBR) method, etc., conducted simultaneously with inserting the implant.

The present invention further provides a fixing member inserted in an alveolar bone or a gnathic bone for an implant which comprises a tube or a pillar made of an hydroxyapatite ceramics at least one part of which is a ceramics porous article consisting essentially of a hydroxyapatite formed by agitation foaming, in which a number of approximately spherical pores mutually contact having pore structures communicated three-dimensionally opened at the contact area and having an averaged porosity of from 65% to 85%.

The usage of the ceramics porous article as the fixing member for an implant promotes regeneration of bone at the implant insertion site because cells intrude and attach within the pores in a short time, and swiftly forms the bone with strength in a degree that it can support the implant inserted inside the tube.

As a preferable embodiment, the present invention provides a fixing member inserted in an alveolar bone or a gnathic bone for an implant which comprises a tube and a pillar made of an hydroxyapatite ceramics, wherein the pillar made of the hydroxyapatite ceramics is disposed inside the tube in a manner that the peripheral surface of the pillar is surrounded at least 70% by the tube, wherein at least one part of both the tube and the pillar are ceramics porous articles consisting essentially of a hydroxyapatite formed by agitation foaming, in which a number of approximately spherical pores mutually contact having pore structures communicated three-dimensionally opened at the contact area and having an averaged porosity of from 65% to 85%, and wherein the averaged porosity of the pillar is greater than the averaged porosity of the tube.

Filling the pillar part made of the hydroxyapatite ceramics with the foregoing ceramics porous article rather than void situation easily maintains the bone formation cells and enables to extremely promote regeneration of bone.

Mesenchymal stem cells, bone marrow cells or osteoblast cells are preferable to be introduced into the tube or the pillar consisting essentially of the hydroxyapatite ceramics. Because the porous article of hydroxyapatite ceramics allows a lot of cells to intrude into it, introducing cells with capability of promoting the generation of bone around the implant insertion site forms bone swiftly, increases the strength of the bone, and also promotes synostosis between the implant and its fixing member.

Further, Platelet Rich Plasma (PRP) is preferable to be introduced into the tube or the pillar consisting of a hydroxyapatite ceramics in order to promote breeding of bone cells and curing of gingiva. Furthermore, it is preferable that Platelet Derived Growth Factor (PDGF), Fibroblast Growth Factor (FGF), Transforming Growth Factor-beta (TGF-β), Hepatocyte Growth Factor (HGF), Bone Morphogenetic Protein (BMP), Vascular Endothelial Growth Factor (VEGF) or Enamel Matrix Derivative (EMDOGAIN®), etc., is introduced into there.

A cross-sectional area perpendicular to the axial direction of the fixing member for the implant is from 1.5 times to 50 times as large as a cross-sectional area perpendicular to the axial direction of the implant. By means of employing the above dimension, even a small fixing member for the implant can fix the implant tightly.

Still further, the present invention provides an implant composite which comprises an implant inserted inside of the tube or into the pillar of the above fixing member for the implant. An early integration between the implant tooth and its fixing member before inserting the implant tooth into bone enables to save an operation in oral cavity, further simplifies, reduces and summarizes the medical treatment because it regenerates own bone that can support the implant tooth stably.

Still further, the present invention provides an implant composite which comprises an umbrella consisting of a hydroxyapatite ceramics formed adjacent a head site of the implant. The above implant composite is also the foregoing integration between the implant and its fixing member enabling to simplify, reduce and summarize the medical treatment. The above implant composite has an effective configuration particularly when the longer implant is inserted at the position where the height of the bone is not enough.

According to the invention, an implant is fixable firmly by a small fixing member.

THE MOST PREFERRED EMBODIMENT TO CARRY OUT THE INVENTION

Preferred embodiments of the present invention will hereinafter be described in detail with reference to the attached drawings.

The present invention provides a method for fixing an implant comprising steps of inserting a ceramics porous article consisting essentially of a hydroxyapatite into an implant insertion site of an alveolar bone or a gnathic bone reinforcing an own bone, and further inserting the implant into the own bone.

In the present invention, the ceramics porous article may further comprises other calcium phosphate based ceramics such as tricalcium phosphate (TCP), etc. Further, it usually takes at least one week and up to about twelve months to augment patients' own bone tissue.

Hydroxyapatite is main composition of bone, comparatively superior in mechanical strength and so on, and is a material that is suitably superior in biocompatibility. Moreover, it also has features that a lapse of several years makes it being absorbed by degrees into living tissue and that it may favorably replace with living bone.

Additionally, a hydroxyl group or a phosphate group of the hydroxyapatite may be partially substituted with a carbonic acid group.

The porous article consisting of the hydroxyapatite ceramics preferably has pore structures in which a number of approximately spherical pores mutually contact communicating three-dimensionally opening at the contact area and has an averaged porosity of at least 65%.

The foregoing pore structure allows cells, blood and so on each forming bone to intrude into inside of the ceramics porous article from the entire direction and enables to promote regeneration of the bone as a whole.

Specifically, it is preferable the fixing method for the implant employs the fixing member for the implant in accordance with the present invention.

Figure 1:
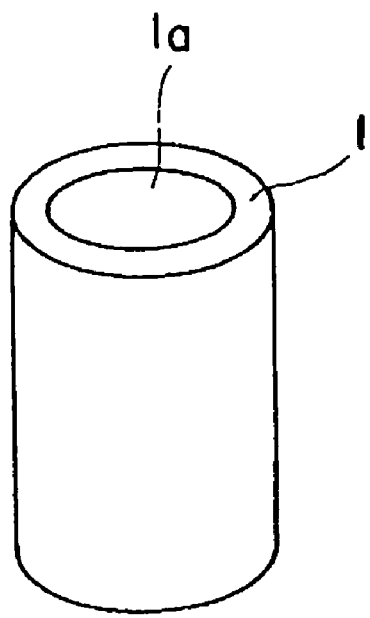
FIG. 1 is a schematic perspective view illustrating one embodiment of a fixing member for an implant in accordance with the present invention.

FIG. 1 is a schematic perspective view illustrating one embodiment of the fixing member for the implant in accordance with the present invention.

In FIG. 1, a tube 1 consisting of hydroxyapatite ceramics composes the fixing member for the implant and an inside 1a of the tube makes a cavity. At least one part, preferably all, of the tube 1 is a ceramics porous article consisting of a hydroxyapatite formed by agitation foaming (or stirring), in which a number of approximately spherical pores mutually contact having pore structures communicated three-dimensionally opened at the contact area and having an averaged porosity of from 65% to 85%.

The usage of the above-described ceramics porous article as the fixing member for the implant promotes regeneration of bone even at the implant insertion site being void because cells intrude within the pores in a short time, and bone tissue consisting of 100% own bone will regenerate between the fixing member for an implant and the implant. Accordingly, bone tissue consisting only of own bone regenerates with good condition at the implant insertion site. Therefore, both the implant consisting of titanium alloy, etc., and the bone tissue can be integrated rigidly and the mechanical strength of the portion should be so increased early as to stably support the implant inserted inside the tube 1.

It is preferable that the averaged porosity of the porous article is at least 65% and up to 85%.

When the averaged porosity is less than 65%, it becomes difficult that the cells intrude and adhere within the fixing member for the implant. Moreover, a circulation of blood, etc., also becomes difficult.

On the other hand, when the averaged porosity exceeds 85%, the fixing member lacks in mechanical strength and tends to break down.

Furthermore, the tube may be replaced with a pillar without a cavity. When the pillar is employed, it may consist of the porous article with entirely uniform porosity or with high porosity having a center portion with local averaged porosity of around 85%.

Further, the tube or the pillar may be preferable to be a right circular tube or a right circular pillar; however, the profile circle is not limited to exactly circular but may be elliptical, etc. Furthermore, the tube may have a bottom. Moreover, plural of the circular tube or the circular pillar may be arranged in a raw to provide a structure enabling to introduce plural of implant tooth.

Although it is preferable that the averaged porosity of the porous article is at least 65% and up to 85%, the tube may be formed in a manner that the porosity increase or decrease inclining towards vertical direction taking workability and mechanical strength of the tube into consideration. Inclination of the porosity may be formed by employing a laminate structure.

For example, the porosity may be settled to increase or decrease continuously or in stepwise towards the growing direction of the teeth from maxillary bone or mandible bone.

Additionally, the porous article in the present invention may be used as an implant composite optionally in combination with an article consisting of compact material of hydroxyapatite ceramics in a standpoint of reinforcement.

For example, a structure consisting of the compact article as the inner part and the porous article as the outer circumferential part enables to support the implant tooth strongly in the inside and promotes bone generation in the outer circumferential part. In the present invention, the compact article capable of supporting the implant is defined as having a porosity of up to 10%. The porosity is preferably up to 5% and desirable to be zero.

Further, it is preferable that the averaged pore diameter of the porous article is at least 150 μm and up to 600 μm. Furthermore, it is preferable that the averaged opening diameter at the communicating area of each pores of the porous article is at least 30 μm.

The averaged pore diameter and the averaged opening diameter as the foregoing description will improve easiness in intrusion of the cells into the implant, and accelerate the intruding rate or breeding rate thereby promoting the regeneration of bone as a whole.

It is preferable that the porous article of hydroxyapatite ceramics thus described is formed by agitation foaming slurry containing the hydroxyapatite.

The agitation foaming enables to easily control the foregoing high porosity, increasing porosity or decreasing porosity, pore properties, etc., which are suitable as a fixing member for the implant; and further enables to obtain the porous article with relatively high mechanical strength.

The agitation foaming further enables to form a compact skeleton (the remaining portion except pores) of the porous article of the hydroxyapatite ceramics with the porosity of 5% or smaller. Furthermore, it induces to form own bone among the pores of the fixing member for the implant and accordingly enables to use the inserted implant semi permanently without decaying the alveolar bone or the gnathic bone adjacent the treated portion again after the treatment. The porosity of the skeleton is preferably 3% or smaller.

As a method for producing the porous article of hydroxyapatite ceramics by means of the above agitation foaming, for example, the method described in U.S. Pat. No. 6,340,648 B1 is employable. The method will be concretely described below:

To begin with, hydroxyapatite powder and cross-linking resin such as polyethyleneimine, and so on are added into a solution of dispersing agent; and then, by agitating and mixing the solution, ingredient slurry is prepared. Subsequently, polyoxyethylene lauryl ether as a foaming agent is added thereto and the resultant slurry is foamed up by mechanical stirring to make the foam uniform and stable resulting in foamed slurry.

Further, a cross-linking agent (gelatinizer) such as sorbitolpolyglycidyl ether is added into the foamed slurry; and then, by agitating and mixing the resultant slurry, porous slurry is prepared. Still further, the porous slurry is introduced into a die, molded and formed to porous gelatinization article (cross-linking article) in the situation maintaining the foamed structure; thereafter sintering it, a ceramics porous article is obtained.

Additionally, regarding the size of the fixing member for the implant in the present invention, the height is about 1 to 25 mm, and the outside diameter is preferably about 2 to 15 mm corresponding to a diameter of the tooth, each depending on the size of the implant tooth or the situation of the patient's bone. In the case where the fixing member for the implant is a tube, the inside diameter of the tube is about 1 to 10 mm.

Moreover, it is preferable that various factors such as cells for promoting generation of bone, bone formation factor, angiogenesis factor and so on are soaked into the surface of the fixing member for the implant of the present invention with the purpose of promoting generation of bone.

Inside 1a of the tube 1 made of the hydroxyapatite ceramics as shown in FIG. 1, the pillar made of the hydroxyapatite ceramics may be disposed in a manner that the peripheral surface of the pillar is surrounded at least 70% by the tube.

In this situation, it is preferable that the pillar may be made of ceramics porous articles consisting of a hydroxyapatite formed by agitation foaming, in which a number of approximately spherical pores mutually contact having pore structures communicated three-dimensionally opened at the contact area, and wherein the averaged porosity of the pillar is greater than the averaged porosity of the tube.

The averaged porosity of the pillar is preferably at least 80%, and more preferably at least 85%. Further, it may be suitable that no distinct border exists between the tube and the pillar, and that the porosity gradually changes between them.

Although the implant tooth should be inserted into the pillar, filling the pillar part with the foregoing ceramics porous article of the hydroxyapatite rather than leaving it void situation easily maintains the bone cells and enables to extremely promote regeneration of bone.

An implant treatment procedure with the use of the above fixing member for the implant will be explained below:

To begin with, drilling a hole into an alveolar bone or a gnathic bone of the patient, inserting the fixing member for the implant into the hole, once closing the hole with his gingiva, and then, sew up his mucosa. In the treatment, the hole with a circular section is easy to be drilled; accordingly, the circular section is suitable for the fixing member for the implant. Additionally, regarding with the fixing member for the implant, it is preferable to select a fixing member for the implant with an appropriate diameter capable of tightly fixing the implant. With a lapse of about 1 to 3 months, bone cells will breed entirely on the fixing member and bone will be formed inside the tube. All or most of this bone is formed of his own bone. This will reinforce the alveolar bone or the gnathic bone. Subsequently, cutting the mucosa at the position where the fixing member for the implant is inserted, drilling a hole again into the site where the bone regenerated inside the tube as the fixing member, and then insert the implant. Closing the hole with the gingiva again, sewing up the mucosa and bond the implant and the bone tight spending about 1 to 3 months.

Afterwards, making the head of the inserted implant expose from the gingiva, attach a foundation for connecting an artificial tooth. Thereafter, taking a conformer of the artificial tooth and putting the artificial tooth on will completely finish the implant treatment.

The reason why it is preferable that the hole is closed with the gingiva and the mucosa is sewed up until the bone is regenerated is because saprophyte invades and tends to breed inducing the fear of causing communicable disease before the bone is formed inside the ceramics porous article when the surface of the fixed member for the implant is exposed condition in oral cavity after it has been inserted into the bone. Further, it is preferable that silver ions with bactericidal action are added to the fixing member for the implant in order to prevent breeding of the saprophyte, and suppress developing of the communicable disease. Furthermore, a membrane method is jointly carried out in order to prevent immersion of epidermic cells and to efficiently regenerate own bone. The membrane method is carried out by applying a membrane with or without absorbency, or by coating a bone wax respectively over the area being in contact with mucosa.

Although the size of the fixing member for the implant will be adjusted appropriately depending on the amount and the condition of the alveolar bone or the gnathic bone at the inserting part of the implant tooth, it is usually about 10 mm in height, and might be entirely inserted into the alveolar bone or the gnathic bone. Further, it is preferable that a layer of the porous article of hydroxyapatite ceramics with the thickness of 1 mm or greater should exist uniformity around the implant in order to sufficiently form the reinforced bone adjacent the implant. Furthermore, it is preferable that the fixing member for the implant might be chamfered off and rounded the corner in order to prevent injuring the gingiva or the mucosa.

Moreover, small slits or linear holes may be optionally provided over the outer circumferential area of the tube as the fixing member for the implant. These will make the bone cells easily intrude into the tube and will enable to promote bone formation.

Figure 2:
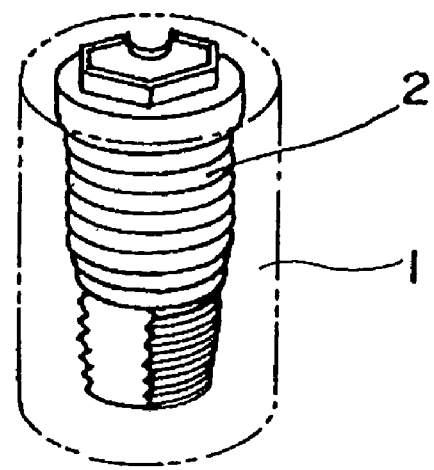
FIG. 2 is a schematic perspective view illustrating one embodiment of an implant composite in accordance with the present invention.

FIG. 2 shows an implant composite in which an implant 2 is preparedly inserted inside a tube 1 as the fixing member for the implant. The implant composite shown in FIG. 2 illustrates an integration of an implant with a fixing member for the implant preparedly before the implant is inserted into a bone.

The implant composite enables to save an operation in oral cavity. Besides, the usage of the fixing member for the implant in accordance with the present invention simplifies, reduces and summarizes the medical treatment because it regenerates own bone that can support the implant stably.

It is preferable that the implant is made of titanium or titanium alloy. Titanium is a metal superior in biocompatibility and mechanical strength, and because the bone cells are easy to fix with the titanium, the implant made of titanium is capable of fixing inside of the tube as the fixing member for the implant.

Further, for the purpose of supporting and fixing the implant stably, it is preferable that the area where the implant is fixed to is only made of bone cells rather than the condition where the hydroxyapatite ceramics and the bone cells mixed each other.

Accordingly, it is suitable that a layer of own bone is formed among a space made between an outer circumferential area of the implant and the hydroxyapatite ceramics composing the fixing member for the implant.

For example, a structure of promoting a formation of own bone may be employable wherein the upper part and the lower part of the implant tooth is in contact with the fixing member for the implant, supporting and fixing them tight by means of screw etc., and wherein a space is made only in a circumferential area of the middle part of the implant, enabling blood and cells to intrude into the space easily.

Figure 3:
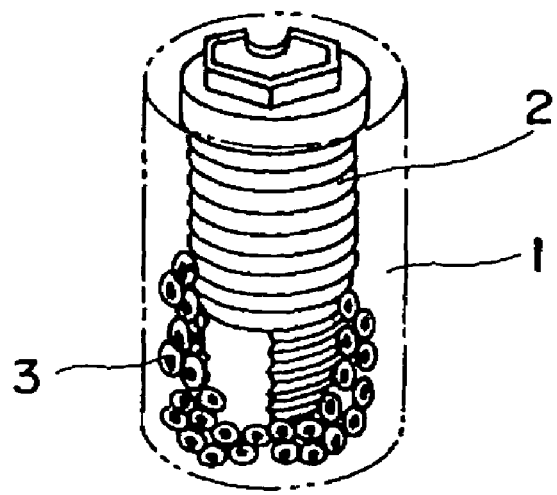
FIG. 3 is a schematic perspective view illustrating another embodiment of the implant composite in accordance with the present invention.
Figure 4:
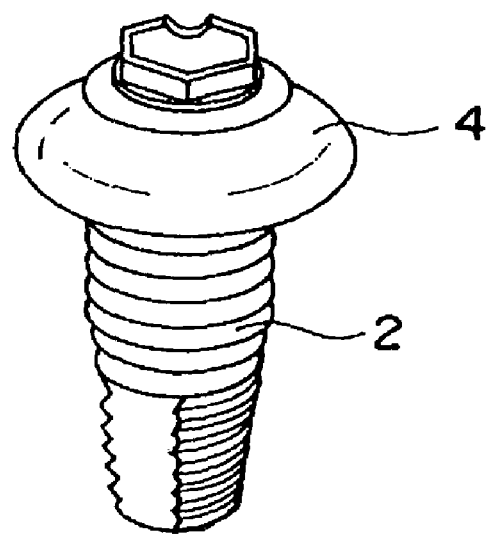
FIG. 4 is a schematic perspective view illustrating still another embodiment of the implant composite in accordance with the present invention.

Additionally, implants 2 shown in FIGS. 2 to 4 are of screw type; however, the configuration of the implant tooth is not limited to them. The implant tooth of screw type is supported and fixed with the whole ridge, and after treatment, it preferably distributes the chewing force over the whole ridge to convey efficiency into bone. In this case, pitch for thread is usually about 0.1 to 2.0 mm.

FIG. 3 is a schematic perspective view illustrating another embodiment of the implant composite in accordance with the present invention. The implant composite as shown in FIG. 3 has a configuration similar with the above implant composite, and cells 3 for promoting bone-formation such as mesenchymal stem cells, bone marrow cells or osteoblast cells are introduced into the tube 1 or into the pillar each made of hydroxyapatite ceramics, and are adhered there.

Because the porous article of hydroxyapatite ceramics allows a lot of cells to intrude into it as described above, introducing cells 3 for promoting bone-formation into the tube 1 or the pillar around the implant 2 forms bone swiftly, increases the strength of the bone, and also promotes synostosis between the implant and its fixing member.

Although typical examples of the cell 3 for promoting bone-formation include mesenchymal stem cells, bone marrow cells, osteoblast cells, and so on, particularly preferable cells are mesenchymal stem cells or osteoblast cells.

In order to regenerate bones earlier, it is preferable that these cells should be applied to live body after they were cultured sufficiently in vitro.

In addition, for the purpose of promoting bone formation similarly, various factors such as bone formation factor, angiogenesis growth factor, Enamel Matrix Derivative (EM-DOGAIN®), etc., or active material such as cytokine, etc., may be soaked into the fixing member for the implant.

Further, introducing Platelet Rich Plasma (PRP) into the fixing member for the implant may be preferable because PRP will be able to promote breeding of bone cells and curing of gingiva still more.

Moreover, introducing artificial blood vessel into the fixing member for the implant enables to further raise the effect of promoting bone-formation.

FIG. 4 is a schematic perspective view illustrating still another embodiment of the implant composite in accordance with the present invention. The implant composite shown in FIG. 4 comprises an umbrella 4 consisting of hydroxyapatite ceramics formed adjacent a head portion of the implant 2. The configuration of the umbrella 4 may be appropriate as a conception of pileus for lamps rather than a conception of an umbrella for rain, and it may be inverted-plate, hemispheric, etc. A bottom plane of the umbrella 4 is formed evenly. Outside diameter of the umbrella 4 is about 3 to 20 mm.

The above implant composites are effective particularly when the longer implant is inserted at the position where the height of the bone is not enough. When the implant composite is inserted into the alveolar bone, the umbrella 4 made of the hydroxyapatite ceramics may be completely inserted into the bone after whittling the bone shallow widely, or may be planted with the situation of being placed on the alveolar bone.

It is preferable that the umbrella 4 consists essentially of the foregoing porous article of the hydroxyapatite ceramics. However, in the case where it is impossible to completely cover the implant composite with mucosa, the upper part of umbrella 4 exposing in oral cavity might be preferably made of the foregoing compact article with few pores to prevent invasion of saprophyte. Further, silver ions having bactericidal action may be contained into the umbrella 4. Furthermore, the umbrella 4 may be applied in combination with the foregoing tube.

Moreover, as another aspect of a method for fixing an implant in the present invention, inserting an implant whose at least one part of the periphery is integrated with a hydroxyapatite ceramics into an implant insertion site of an alveolar bone or a gnathic bone may be employed. For example, in Guided Bone Regeneration (GBR) procedure, an area where the bone formation is desired might be covered with GBR membrane simultaneously with inserting the implant for the purpose of suppressing breeding of gingiva towards bone side. In this occasion, the porous article of the hydroxyapatite ceramics should be disposed around the implant exposed without being completely covered by the GBR membrane.

The exposed surface of the porous article of the hydroxyapatite ceramics may be formed of the foregoing ceramics compact article from a viewpoint of preventing invasion of saprophyte. Moreover, the porous article of the hydroxyapatite ceramics may be disposed inside of the GBR membrane. As thus described, a joint usage of the hydroxyapatite ceramics with the GBR procedure enables to further promote regeneration of bone.

Additionally, in the case where the implant is inserted in the fixing member for the implant, or in the case where the implant is preparedly inserted in the implant composite, it is preferable that a cross-sectional area of the fixing member for the implant is from 1.5 times to 50 times as large as a cross-sectional area of the implant. When the cross-sectional area of the fixing member for the implant is smaller than 1.5 times as large as a cross-sectional area of the implant, the effect of using the fixing member for the implant is unable to be achieved. On the contrary, when it exceeds 50 times, the fixing member for the implant becomes too large to evade inconveniences of charging burdens for the patient or of delaying regeneration of bone. It is more preferable that the cross-sectional area of the fixing member for the implant is from 5 times to 36 times as large as the cross-sectional area of the implant.

INDUSTRIAL APPLICABILITY

As the foregoing description, in accordance with the present invention, the implant treatment should be carried out effectively because a compensation or a reproduction and so on of the alveolar bone or the gnathic bone can be promoted, the bone tissue is strengthened, and the strength of the bone tissue can be increased swiftly to a degree of stably supporting the implant tooth.

Moreover, the fixing member for the implant or the implant composite each in accordance with the present invention induces to form own bone approximately 100% among the pores of the fixing member for the implant and accordingly enables to use the inserted implant semi permanently without decaying the alveolar bone or the gnathic bone adjacent the treated site again after the treatment.

Still further, only the bones concentrated at the area where the implant is inserted and at the peripheral area are possible to be strengthened, and they can be strengthened at an adequate place with high accuracy by means of an operation with a small scale and with little burden on the patient.

It is further understood by those skilled in the art that the foregoing description is a preferred embodiment of the invention and that various changes and modifications may be made in the invention without departing from the spirit and scope thereof.

What is claimed is:

1. A dental implant fixing member, which is adapted to be inserted in an alveolar bone or a gnathic bone, said fixing member comprising:

a tube made of a hydroxyapatite ceramic, wherein at least a portion thereof is porous, the tube:
  (i) consisting essentially of a hydroxyapatite formed by agitation foaming, in which tube a number of approximately spherical pores mutually contact, open at the contact area, and communicate three-dimensionally; and
  (ii) having an average porosity of from 65% to 85%, an average pore diameter of between 150 μm and 600 μm, an average opening diameter of the three-dimensionally communicated pores at the contact area of at least 30 μm; and a pillar which is a ceramic porous article consisting essentially of a hydroxyapatite formed by agitation foaming, in which pillar a plurality of approximately spherical pores mutually contact, open at the contact area, and communicate three-dimensionally, wherein the average porosity of the pillar is greater than the average porosity of the tube, wherein the pillar is disposed inside the tube in a manner that a peripheral surface of the pillar is surrounded by at least 70% of the tube, and wherein a cavity is provided in the fixing member so as to fix the implant therein.

2. The fixing member for an implant according to claim 1, wherein mesenchymal stem cells, bone marrow cells or osteoblast cells are introduced into said tube or said pillar consisting essentially of the hydroxyapatite.

3. The fixing member for an implant according to claim 1, wherein Platelet Rich Plasma (PRP) is introduced into said tube or said pillar consisting essentially of the hydroxyapatite.

4. The fixing member for an implant according to claim 2, wherein Platelet Rich Plasma (PRP) is introduced into said tube or said pillar consisting essentially of the hydroxyapatite.

5. The fixing member for an implant according to claim 1, wherein one or more of Platelet Derived Growth Factor (PDGF), Fibroblast Growth Factor (FGF), Transforming Growth Factor-beta (TGF-β), Hepatocyte Growth Factor (HGF), Bone Morphogenetic Protein (BMP), Vascular Endothelial Growth Factor (VEGF) and Enamel Matrix Derivative is introduced into said tube or said pillar consisting essentially of the hydroxyapatite.

6. The fixing member for an implant according to claim 1, wherein a cross-sectional area perpendicular to the axial direction of said fixing member for the implant is from 1.5 times to 50 times as large as a cross-sectional area perpendicular to the axial direction of said implant.

* * * * *